(12) United States Patent
Fujimoto et al.

(10) Patent No.: US 7,002,162 B1
(45) Date of Patent: Feb. 21, 2006

(54) INSTRUMENT FOR MEASURING LIFETIME OF FLUORESCENE

(75) Inventors: Masatoshi Fujimoto, Hamamatsu (JP); Shinichiro Aoshima, Hamamatsu (JP); Makoto Hosoda, Hamamatsu (JP); Yutaka Tsuchiya, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 261 days.

(21) Appl. No.: 10/344,850

(22) PCT Filed: Aug. 18, 2000

(86) PCT No.: PCT/JP00/05549

§ 371 (c)(1),
(2), (4) Date: Feb. 19, 2003

(87) PCT Pub. No.: WO02/16913

PCT Pub. Date: Feb. 28, 2002

(51) Int. Cl.
*G01N 21/64* (2006.01)

(52) U.S. Cl. .................................. 250/458.1; 359/258
(58) Field of Classification Search ............. 250/458.1; 359/258

See application file for complete search history.

(56) References Cited

U.S. PATENT DOCUMENTS 5,828,484 A * 10/1998 Ho et al. .................... 359/258

FOREIGN PATENT DOCUMENTS

| JP | 63-053443 | 3/1988 |
| JP | 03-289540 | 12/1991 |
| JP | 06-174640 | 6/1994 |
| JP | 09-189612 | 7/1997 |
| JP | 10-048044 | 2/1998 |
| JP | 10-206234 | 8/1998 |
| WO | WO 95/10034 | 4/1995 |

* cited by examiner

*Primary Examiner*—David Porta
*Assistant Examiner*—Shun Lee
(74) *Attorney, Agent, or Firm*—Drinker Biddle & Reath LLP

(57) ABSTRACT

A fluorescence component that passes through a region of a detection medium where a change in refractive index has been induced through a nonlinear optical effect produced in the detection medium by a gate pulse is observed as a fluorescence image by utilizing a change in polarization state. By observing the change in position of the fluorescence image while correlating with the change over time in the fluorescence, a fluorescence lifetime measuring apparatus is realized with which the change over time in the fluorescence, in particular the fluorescence lifetime, can be measured efficiently with high temporal resolution.

27 Claims, 12 Drawing Sheets

INSTRUMENT FOR MEASURING LIFETIME OF FLUORESCENE

TECHNICAL FIELD

The present invention relates to a fluorescence lifetime measuring apparatus that can observe fluorescence emitted from a substance after irradiation with a light pulse.

BACKGROUND ART

With the development of laser technology with regard to femtosecond-domainultra-shortpulse lasers and the like, in recent years attention has focused on various phenomena that occur with a femtosecond time domain or on a femtosecond time-scale. One such phenomenon is the phenomenon of fluorescence emitted by a substance upon irradiation with a light pulse.

If a substance is irradiated with such a femtosecond ultra-short light pulse, then fluorescence that changes over time with a femtosecond time domain can be obtained, for example the behavior of the fluorescence phenomenon on a femtosecond time-scale can be obtained. Examples of techniques carried out to observe such a fluorescence phenomenon are a method using a streak camera and a method of sampling measurement through pumping and probing.

DISCLOSURE OF THE INVENTION

To measure the fluorescence phenomenon with a femtosecond time domain, a fluorescence measurement method for which high temporal resolution of femtosecond order can be realized is required. However, with conventional measurement methods such as those mentioned above, measurement cannot be carried out with sufficient temporal resolution.

That is, with the measurement method using a streak camera (e.g. Japanese Patent Application Laid-open No. H10-48044), it is difficult to carry out fluorescence measurement with a temporal resolution better than 100 femtoseconds. Moreover, it is difficult to adjust and match the timing of the streak sweeping for each measurement to femtosecond order. With such a time domain, it is thus not possible to use a method in which reliable measurement results are obtained by carrying out measurement a plurality of times and totaling the measurement results. This is a problem in particular with measurement such as fluorescence measurement in which extremely faint light is the subject of observation.

As a measurement technique with high temporal resolution based on the measurement method using a streak camera, there is a method using an optical Kerr gate (e.g. Japanese Patent Application Laid-open No. H9-189612). With this method, light is made to be incident on a medium exhibiting a large optical Kerr effect, and fluorescence that has been suitably polarized is made to be incident on the medium from another direction; time-resolved measurement of the fluorescence is carried out by observing the change in the polarization. In this case, the duration of the birefringence at the Kerr gate which exhibits a large Kerr effect is long and superimposition of the physical properties of the medium occurs, and hence the precision is worse than measurement using a streak camera, and thus it is not possible to carry out measurement of changes over time with high temporal resolution. Moreover, there are many other problems such as it not being possible to carry out measurement unless the optical signal is strong.

Moreover, with sampling measurement through pumping and probing, measurement with high temporal resolution is possible. However, with this method only repetitive phenomena can be measured. Moreover, observation of a phenomenon is possible only at a fixed time in each measurement, and hence to observe the temporal changes and temporal evolution of a phenomenon such as fluorescence, it is necessary to carry out measurements over an extremely long time period. In particular, in this case a problem arises in which the measurement conditions change over time, for example when the light source is unstable and there is a large drift over time, and hence it becomes difficult to carry out measurements with high precision.

The present invention has been produced to resolve the problems described above; it is an object of the present invention to provide a fluorescence lifetime measuring apparatus that can carry out observation of a fluorescence phenomenon and measurement of the fluorescence lifetime efficiently with high temporal resolution.

To attain this object, the fluorescence lifetime measuring apparatus according to the present invention comprises a light source part that produces, from a light pulse supplied by a pulse light source, and outputs a first light beam and a second light beam having output timing synchronized with one another, a detection medium that exhibits birefringence in a pulse position of a light pulse in accordance with the intensity thereof, a gate optical system that forms a gate pulse based on the first light beam and causes the gate pulse to be incident on the detection medium, an excitation optical system that forms an excitation pulse based on the second light beam and causes the excitation pulse to be incident on a substance undergoing measurement to generate fluorescence, a fluorescence optical system that irradiates the fluorescence from the substance undergoing measurement onto a prescribed region of the detection medium that includes a light track region in which a change in refractive index has been induced through an on linear optical effect due to the gate pulse being incident on the detection medium, and a photodetection part that detects the fluorescence that has passed through the prescribed region of the detection medium, wherein the gate optical system comprises gate pulse polarizing means for putting the gate pulse into a prescribed polarization state, and an incidence optical system that causes the gate pulse to be incident on the detection medium according to prescribed incidence conditions, the fluorescence optical system comprises fluorescence polarizing means for putting the fluorescence into a prescribed polarization state, and the photodetection part comprises analyzing means that transmits only a prescribed polarized component out of the fluorescence that has passed through the prescribed region of the detection medium, photodetection means that detects and observes the fluorescence that has been transmitted through the analyzing means, and image-forming means that forms the fluorescence that has passed through the prescribed region of the detection medium and been transmitted through the analyzing means into an image on the photodetection means to produce a fluorescence image, whereby the change over time in the fluorescence is measured from the fluorescence image by utilizing the movement with time of the pulse position where birefringence is exhibited in the light track region.

With the development of laser technology with regard to high-intensity ultra-short pulse lasers and the like, nonlinear optical effects of substances such as an optical Kerr effect arising through laser light that has a higher intensity than normal light, and various phenomena caused by these nonlinear optical effects have become problems. That is, the nonlinear susceptibility of a substance to high-order terms of second order and above of an electric field is lower in value than the first order term, and hence with normal light only a linear response is observed. On the other hand, with light having a sufficiently large intensity (electric field) such as laser light, effects due to such nonlinear terms of second order and above appear.

As phenomena due to such nonlinear optical effects, for example a self-focusing effect of light that arises upon irradiating a substance with a high-intensity light pulse, and self-trapping effects such as channeling and filamentation in which light propagates with the beam diameter remaining narrow are known. Moreover, it is possible to observe the light track of a light pulse using such a phenomenon.

With the fluorescence lifetime measuring apparatus described above, this light track observation method is used in observation of a fluorescence phenomenon. That is, using a pulse light source such as a high-intensity femtosecond laser, which is an ultra-short pulse light source, a gate pulse for observing the fluorescence and an excitation pulse for exciting the fluorescence are produced from two light beams outputted from the pulse light source. The gate pulse, and the fluorescence generated by the substance undergoing measurement through the excitation pulse are then put into prescribed polarization states and respectively made to be incident on and irradiated onto the detection medium. Here, due to the incidence of the gate pulse, a region is formed in the detection medium where birefringence is exhibited in which the refractive index changes and anisotropy arises in the refractive index through a nonlinear optical effect, this region corresponding to the pulse position of the gate pulse at each time.

A component for which the polarization state has changed due to this out of the fluorescence that has passed through the detection medium is selected by the analyzing means and detected by the photodetection means. As a result, a fluorescence image that is produced due to the birefringence which moves with time as the gate pulse propagates through the detection medium, and whose position is correlated to the time when the fluorescence was emitted can be obtained.

The gate pulse for producing the fluorescence image in the detection medium is a short-time-width light pulse from a pulse light source as stated above. It is thus possible to make the positions of the fluorescence image and the times in the temporal change of the fluorescence phenomenon correspond to one another with high precision. Consequently, by observing the change in position (positional dependence) of the intensity or the like of the fluorescence image, the change over time (time dependence) of the fluorescence phenomenon can be measured efficiently with high temporal resolution, and hence it becomes possible to determine the fluorescence lifetime with high temporal resolution.

With such a measurement method, there is very little timing jitter, and hence fluorescence can be measured all in one go over a certain time range, and with high temporal resolution, for example femtosecond temporal resolution. Moreover, because measurement can be carried out efficiently through a single shot with one measurement, the measurement time can be short, and moreover deterioration of the precision through changes in the operating conditions of the apparatus and so on can be suppressed.

Moreover, regarding the detection medium, for example a substance that can efficiently give rise to a nonlinear optical effect should be selected and used; in particular, it is preferable to use a substance comprising a gas or a liquid for which the response speed of the nonlinear optical effect is fast, whereby the temporal resolution can be increased.

BEST MODE FOR CARRYING OUT THE INVENTION

Figure 1:
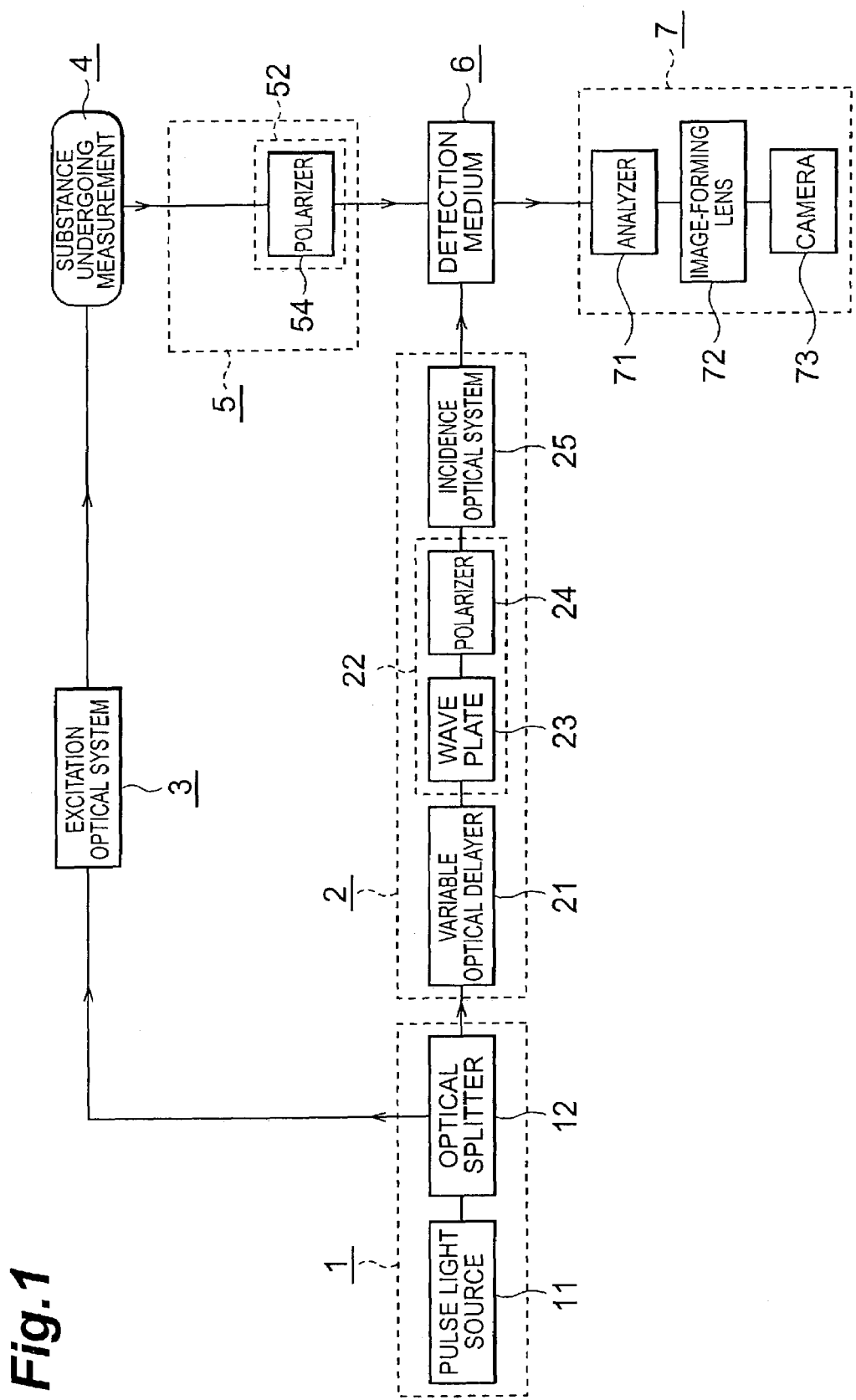
FIG. 1 is a block diagram showing a first embodiment of a fluorescence lifetime measuring apparatus.

Following is a detailed description of preferable embodiments of the fluorescence lifetime measuring apparatus according to the present invention, along with the drawings. Note that in the description of the drawings, elements that are the same as one another are given the same reference numeral, and redundant repeated description is omitted. Moreover, the ratios of dimensions in the drawings do not necessarily match those in the description.

FIG. 1 is a block diagram showing a first embodiment of the fluorescence lifetime measuring apparatus according to the present invention. The fluorescence lifetime measuring apparatus in the present embodiment is constituted from a light source part 1, a gate optical system 2, an excitation optical system 3, a fluorescence optical system 5, a detection medium 6, and a photodetection part 7.

The light source part 1 has an ultra-short pulse light source 11 that produces and outputs a light pulse, and an optical splitter 12. The light pulse outputted from the ultra-short pulse light source 11 is split by the optical splitter 12 into a first light beam that is led to the gate optical system 2, and a second light beam that is led to the excitation optical system 3.

The first light beam and the second light beam outputted from the light source part 1 are taken as a gate pulse and an excitation pulse respectively, and are led to the detection medium 6 and a substance under going measurement 4 respectively.

The gate optical system 2 forms the gate pulse based on the first light beam from the light source part 1, and causes the gate pulse to be incident on the detection medium 6 from a prescribed axis of incidence. The gate optical system 2 has a variable optical delayer 21 for setting and changing the time delay difference between the gate optical system 2, and the excitation optical system 3 and the fluorescence optical system 5, gate pulse polarizing means 22 that comprises a wave plate 23 and a polarizer 24 and is for putting the gate pulse into a prescribed polarization state, and an incidence optical system 25 that causes the gate pulse to be incident on the detection medium 6 according to prescribed incidence conditions.

The excitation optical system 3, on the other hand, forms the excitation pulse based on the second light beam from the light source part 1, and causes the excitation pulse to be incident on the substance undergoing measurement 4 from a prescribed axis of incidence. Fluorescence which is generated in the substance undergoing measurement 4 through the excitation pulse and which is the subject of the change-over-time measurements using the present apparatus is irradiated onto the detection medium 6 by the fluorescence optical system 5 from a prescribed axis of irradiation. The fluorescence optical system 5 has fluorescence polarizing means 52 that comprises a polarizer 54 and is for putting the fluorescence into a prescribed polarization state.

With the constitution described above, the gate pulse is focused and made to be incident on the detection medium 6 through the gate optical system 2. At this time, the condensed gate pulse forms a high-intensity, high-density light beam in a prescribed region inside the detection medium 6, and in this pulse position a change in the refractive index inside the detection medium 6 is induced through a nonlinear optical effect such as an optical Kerr effect. The region in which this change in refractive index occurs and which thus exhibits birefringence corresponds to the spatial region in which the light of the gate pulse is distributed, and hereinafter is referred to as the light track region. The position of this light track region varies with time due to the movement of the light pulse position of the gate pulse that forms the light track region. Light track region position information thus corresponds to time information.

Here, if the fluorescence from the substance undergoing measurement 4 is irradiated via the fluorescence optical system 5 onto a prescribed region of the detection medium 6 including the light track region, then due to the anisotropy of the refractive index in the light track region (birefringence), at each time the polarization state of only the fluorescence component that has passed through the light track region changes relative to that of a fluorescence component that has passed through a region of the detection medium 6 other than the light track region. By observing this changed light component using the photodetection part 7, the fluorescence image generated due to the light track region is measured.

The pulse position of the light track region in the detection medium 6 moves with time as the gate pulse propagates, and hence the position of the above-mentioned fluorescence image varies according to the time of passing through the detection medium 6. By observing the overall fluorescence image formed from the fluorescence images that appear in different positions at different times in this way, and the positional change and distribution of the intensity and so on thereof, the change over time in the fluorescence generated in the substance undergoing measurement 4 can be measured, and hence measurement of the fluorescence lifetime and so on becomes possible.

The photodetection part 7 has an analyzer 71 that transmits only a prescribed polarized component out of the fluorescence that has passed through the prescribed region of the detection medium 6, an image-forming lens 72 that forms the fluorescence component that has been transmitted by the analyzer 71 into an image and thus produces the fluorescence image that will be observed, and a camera 73, which is photodetection means for observing the fluorescence image formed. The fluorescence component that has passed through the light track region is thus selectively transmitted by the analyzer 71, and this fluorescence component is picked up by the camera 73; the change over time in the fluorescence is measured from the fluorescence images obtained.

Note that in the embodiment described above, the gate pulse polarizing means 22 is constituted from the wave plate 23 and the polarizer 24, and the fluorescence polarizing means 52 is constituted from the polarizer 54, but this merely shows one example of the constitutions of the polarizing means 22 and 52. Regarding these constitutions, depending on the polarization states of the light beam and the fluorescence inputted into the gate optical system 2 and the fluorescence optical system 5, and the set polarization states of the gate pulse and the fluorescence, different constitutions can be used, for example a constitution comprising only a wave plate.

Moreover, as the incidence optical system in the gate optical system 2, an incidence optical system 25 that focuses the gate pulse and causes the gate pulse to be incident on the detection medium 6 has been used, but depending on measurement conditions such as the intensity of the gate pulse and the choice of the substance used as the detection medium 6, an optical system that does not carry out focusing may be used as the incidence optical system.

Moreover, in the case that it is necessary for the measurement, for example when the axis of incidence of the excitation pulse onto the substance undergoing measurement 4 and the axis of irradiation of the fluorescence onto the detection medium 6 are approximately on the same axis, excitation pulse removing means comprising an interference filter, a mirror or the like may be further provided in the fluorescence optical system.

Figure 2:
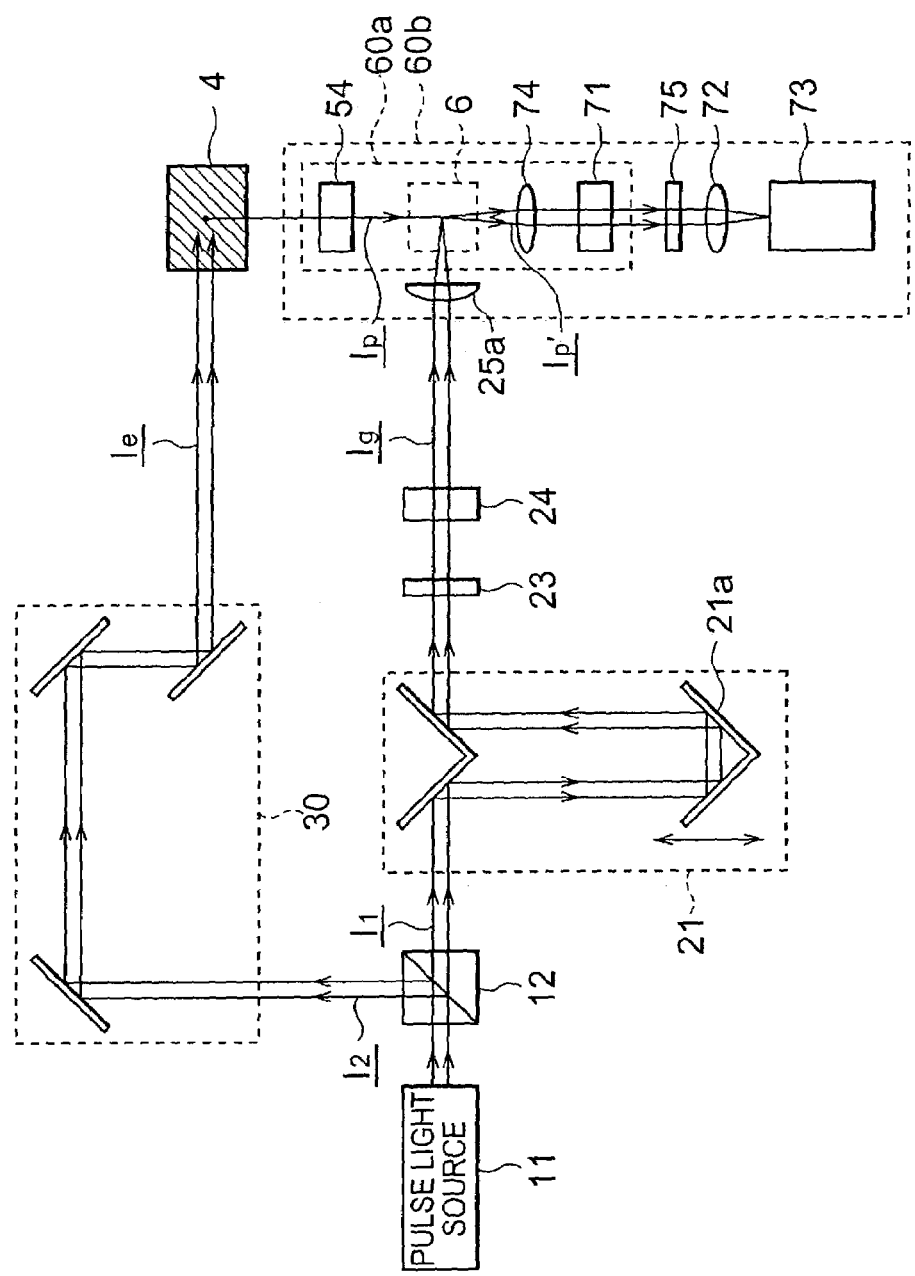
FIG. 2 is a configuration diagram showing an example of the fluorescence lifetime measuring apparatus according to the embodiment shown in FIG. 1.

FIG. 2 is a configuration diagram showing a specific example of the fluorescence lifetime measuring apparatus according to the embodiment shown in FIG. 1.

In the present example, a titanium-sapphire laser having a wavelength of 800 nm, a pulse width of 100 fs, and an energy per pulse of 7 mJ is used as the ultra-short pulse light source 11. The light pulse from the pulse light source 11 is split into a first light beam 11 and a second light beam 12 by the optical splitter 12, which comprises, for example, a half mirror. Here, the light pulse has linear polarization in a horizontal direction relative to the plane of the paper in FIG. 2, i.e. the plane containing the axis of irradiation of the fluorescence from the substance undergoing measurement 4 onto the detection medium 6, the axis of incidence of the excitation pulse onto the substance undergoing measurement 4, and the axis of incidence of the gate pulse onto the detection medium 6, described below (hereinafter referred to as the 'detection plane').

If necessary, a wave plate or the like may be provided between the pulse light source 11 and the optical splitter 12. In this case, for example a prism-type polarization beam splitter can be used as the optical splitter 12.

The first light beam $l_1$ is taken as the gate pulse $l_g$ and is led to the detection medium 6 by the gate optical system. The second light beam $l_2$, on the other hand, is taken as the excitation pulse $l_e$ and is led to the substance undergoing measurement 4 by the excitation optical system. Furthermore, fluorescence $l_p$ that is generated in the substance undergoing measurement 4 through the excitation due to the incidence of the excitation pulse $l_e$ and emitted is led to the detection medium 6 by the fluorescence optical system.

The timing of the incidence and irradiation of the gate pulse $l_g$ and the fluorescence $l_p$ on the detection medium 6 is set or changed using the variable optical delayer 21 in the gate optical system, and an optical path portion 30 in the excitation optical system through which is led the excitation pulse $l_e$ for generating the fluorescence $l_p$.

The optical path portion 30 of the excitation optical system is set and fixed when the apparatus is built, and thus functions as an optical delayer with a fixed time delay, and is used to adjust and set the initial condition of the optical path length difference with the gate optical system and the resulting time delay difference. The variable optical delayer 21 of the gate optical system, on the other hand, is constituted from a movable right-angled mirror 21a; the constitution is such that the optical path length is changed by moving this movable right-angled mirror 21a, whereby the optical path length difference with the excitation optical system and the resulting time delay difference can be changed and set.

The polarization states of the gate pulse $l_g$ and the fluorescence $l_p$ are respectively set using the wave plate 23 and the polarizer 24, which constitute the gate pulse polarizing means in the gate optical system, and the polarizer 54, which is the fluorescence polarizing means in the fluorescence optical system.

The wave plate 23 of the gate pulse polarizing means is a ½-wave plate in the present embodiment. After passing through the variable optical delayer 21, the first light beam $l_1$ has the direction of linear polarization thereof rotated by 90° by the ½-wave plate 23, and is thus converted so as to have linear polarization perpendicular to the detection plane, and then passes through the polarizer 24, which transmits only the component having the perpendicular linear polarization. As a result, a gate pulse $l_g$ having linear polarization perpendicular to the detection plane is obtained. Note that the polarizer 24 is for selecting the component having the perpendicular linear polarization with increased certainty, and a constitution in which the polarizer 24 is not installed can also be adopted.

The fluorescence $l_p$ produced by the substance undergoing measurement 4 through the excitation pulse $l_e$, on the other hand, passes through the polarizer 54, which transmits only a component having linear polarization inclined by 45° to the detection plane. As a result, fluorescence $l_p$ having linear polarization inclined by 45° to the detection plane is obtained.

The gate pulse $l_g$ and the fluorescence $l_p$ obtained as described above are respectively made to be incident on and irradiated onto the detection medium 6 along a prescribed axis of incidence and axis of irradiation. Air at normal temperature and atmospheric pressure is used as the detection medium 6. Note, however, that in the example shown in FIG. 2, the apparatus as a whole is installed in an air atmosphere, and hence a portion of this air in a prescribed region is used as the detection medium 6 as is.

The gate pulse $l_g$ from the gate optical system passes through a focusing lens 25a, which is a plano-convex lens of focal length 200 mm, and is thus incident on the detection medium 6, which is air, along the prescribed axis of incidence while being condensed. Due to the interaction between the gate pulse $l_g$ and the air in the detection medium 6, a light track region in which a nonlinear optical effect such as an optical Kerr effect arises is produced. The refractive index of the detection medium 6 changes within this light track region, and in particular anisotropy (birefringence) arises in the refractive index in a plane perpendicular to the axis of irradiation of the fluorescence $l_p$.

The fluorescence $l_p$ is irradiated from the fluorescence optical system onto a prescribed region of the detection medium 6 including the light track region, with the axis of irradiation being made to be an axis perpendicular to the axis of incidence of the gate pulse $l_g$. The transmitted fluorescence $l_p'$, which is the component of the fluorescence $l_p$ transmitted by the detection medium 6, is detected by the photodetection part.

The transmitted fluorescence $l_p'$ passes through an objective lens 74 and is incident on the analyzer 71. The analyzer 71 is constituted so as to transmit, out of the transmitted fluorescence $l_p'$, only a linearly polarized component that is orthogonal to the linear polarization of the fluorescence $l_p$ that was irradiated onto the detection medium 6. Consequently, only a component of the transmitted fluorescence $l_p'$ that has passed through the light track region and thus had its polarization state changed by the refractive index anisotropy within the light track region is transmitted by the analyzer 71, with a component of the transmitted fluorescence $l_p'$ that has passed through a region of the detection medium 6 where refractive index anisotropy due to the nonlinear optical effect has not occurred not being transmitted by the analyzer 71.

That is, each position of the fluorescence image due to a component of the transmitted fluorescence $l_p'$ that has passed through the analyzer 71 corresponds to a position of the light track region where a change in refractive index has been induced through the nonlinear optical effect when the fluorescence $l_p$ passed through the detection medium 6. Moreover, this position of the light track region moves with time as the gate pulse propagates. The positions of the fluorescence image obtained thus correspond to times, and hence the fluorescence image and the change in position (positional dependence) thereof, when looked at as a whole, correspond to the fluorescence $l_p$ and the change over time (time dependence) thereof.

The fluorescence image due to the component of the transmitted fluorescence $l_p'$ that has passed through the analyzer 71 is formed by the image-forming lens 72 into an image on the CCD camera 73 and is picked up, and as a result the change over time in the fluorescence $l_p$ as the gate pulse $l_g$ moves is measured as a fluorescence image. Note that in the present example an objective lens 74 having a magnification of 10× is used, and measurement is carried out with the focal point of the camera lens of the CCD camera 73 set to infinity.

Moreover, the CCD camera 73 used has 640 (horizontal) ×480 (vertical) pixels and is such that 8-bit intensity data is obtained; to reduce the influence of the scanning line, the CCD camera 73 was installed inclined at 90° to the detection plane such that the vertical direction of the pixel structure was aligned with the direction of propagation of the gate pulse $l_g$ in the detection medium 6 (the direction of the axis of incidence). With these conditions, the distance at the observation plane corresponding to the pixel spacing of the CCD camera 73 is 4.8 µm, which corresponds to a time-scale of 16 fs per pixel.

Moreover, with the measurement apparatus shown in FIG. 2, the gate pulse $l_g$ is condensed into a very small region within the detection medium 6, and hence accompanying this the air undergoes breakdown to produce an air plasma, and thus plasma emission occurs. This plasma emission is white light having spectral components over a broad range.

To eliminate the influence of this emission, an interference filter 75 that corresponds to a suitable wavelength for removing spectral components out of the fluorescence $l_p$ that are not the subject of measurement (not of interest) is installed between the analyzer 71 and the image-forming lens 72.

Regarding the spectral component that is the subject of the measurement described above, on the other hand, before the measurement of the fluorescence lifetime, measurement was carried out without irradiating the fluorescence $l_p$ but with other conditions set to be the same as the conditions during observation, and by subtracting the image data for these measurement results from the image data for the measurement results when the fluorescence was observed, selective observation of the fluorescence image due to the transmitted fluorescence $l_p'$ was carried out. Note, however, that it is also possible to carry out measurement under conditions for which plasma emission does not accompany the gate pulse $l_g$, and in this case the subtractive processing of the image data described above need not be carried out. Moreover, the setting of the spectral component out of the fluorescence $l_p$ that is the subject of measurement can be changed by, for example, changing the interference filter 75.

Moreover, the energy of the gate pulse $l_g$ per pulse was 3.5 mJ immediately before the focusing lens 25a due to loss in the optical elements and so on. Measurement of the change over time in the fluorescence $l_p$ was actually carried out using the fluorescence lifetime measuring apparatus according to the example shown in FIG. 2, but with this observation, the gate pulse $l_g$ was further attenuated using an ND filter, and observation was carried out at 11.0 mJ per pulse.

Following is a description of the effects of the fluorescence lifetime measuring apparatus according to the present invention, along with the results of observation carried out using the apparatus configuration and observation conditions according to the example described above. With this fluorescence lifetime measuring apparatus, an ultra-short pulse laser capable of outputting an ultra-short light pulse was used as the pulse light source 11, and the ultra-short pulse light beam was split using the optical splitter 12, thus forming the gate pulse $1_g$ used in the observation of the fluorescence $l_p$, and the excitation pulse $l_e$ used in the excitation of the fluorescence $l_p$.

By using an ultra-short pulse having an extremely short light pulse time width in this way, the change in position of the fluorescence image and the change over time in the fluorescence can be made to correspond to one another with high precision, and hence it becomes possible to measure the change over time in the fluorescence with high temporal resolution through the observed fluorescence image, and thus the fluorescence lifetime can be determined with high precision. Moreover, by using the ultra-short pulse split into two, precise synchronization of the timing of the incidence and irradiation on the detection medium 6 of the gate pulse $l_g$ and the fluorescence $l_p$ produced through the excitation pulse $l_e$ can be realized.

In particular, by using a light pulse having a sufficiently short time width, for example a pulse width of the ultra-short pulse of 100 fs, in the example described above, it becomes possible for the first time to directly observe as a two-dimensional image a light track image that more-or-less corresponds to the spatial distribution of the light of the gate pulse $l_g$ at a specific time. With the fluorescence image formed by the image of the fluorescence $l_p$ which is produced and moves in accordance with the movement of the gate pulse $l_g$, measurement of the change over time in the fluorescence $l_p$ can thus be carried out with high temporal resolution more-or-less corresponding to the time width of the light pulse used as the gate pulse $l_g$.

Furthermore, in the embodiment described above, the gate optical system 2 has a variable optical delayer 21, and using this the mutual timing between the incidence of the gate pulse $l_g$ and the irradiation of the fluorescence $l_p$ can be changed. In this case, a change in the timing becomes a change in the position of the gate pulse $l_g$ in the direction of the axis of incidence when the fluorescence $l_p$ is irradiated. By changing the mutual timing as appropriate, it is thus possible to make the portion of the fluorescence image for a time range for which one wishes to measure the change over time in the fluorescence $l_p$ be in the measurement field, and thus progressively obtain the required data.

Figure 3:
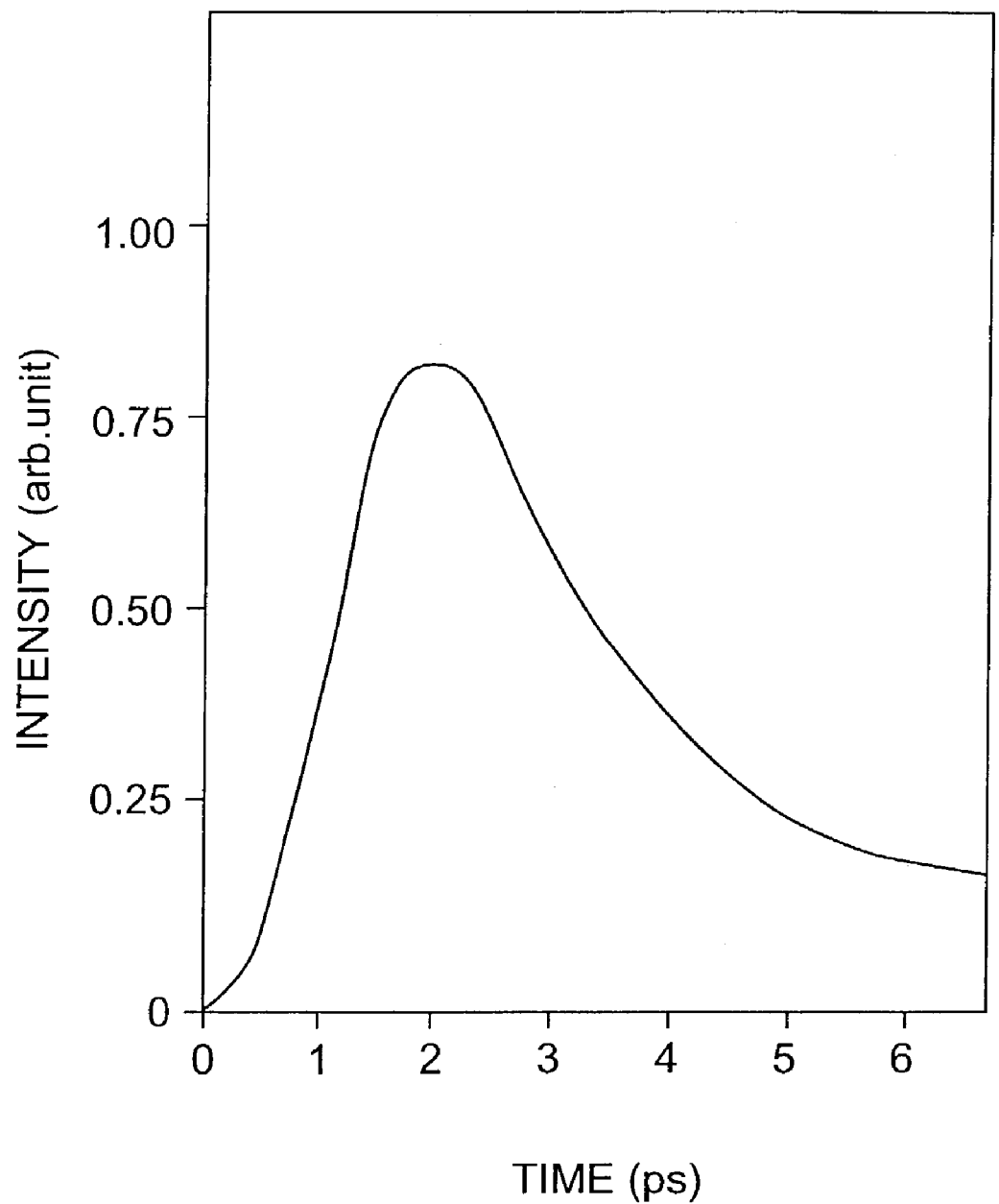
FIG. 3 is a graph showing schematically the change over time in fluorescence measured using the fluorescence lifetime measuring apparatus shown in FIG. 2.

FIG. 3 shows schematically the change over time in the fluorescence $l_p$ as observed from the fluorescence image due to the gate pulse $l_g$ in this way. The horizontal axis shows the arrival time of the fluorescence $l_p$. The vertical axis, on the other hand, shows the intensity of the fluorescence $l_p$ at each time. Here, FIG. 3 is obtained from the two-dimensional image obtained by the CCD camera 73, by summing the image data in the direction perpendicular to the axis of incidence of the gate pulse $l_g$ to convert into a one-dimensional image in the direction of the axis of incidence of the gate pulse $l_g$ (which corresponds to the time axis of the measurement), i.e. the direction of propagation of the gate pulse $l_g$ (hereinafter this one-dimensional image is referred to as the 'computed image'), and then displaying the intensity for each measurement point.

Moreover, regarding obtaining the arrival time of the fluorescence $l_p$ shown on the horizontal axis in FIG. 3, by correlating each measurement position in the above-mentioned computed image to the time at which the gate pulse $l_g$ arrives at that position, the respective positions of the fluorescence image due to the gate pulse $l_g$ are converted into the respective times of the fluorescence phenomenon.

From FIG. 3, it can be seen that, using the fluorescence lifetime measuring apparatus according to the present invention, the appearance of the change over time in the fluorescence emitted from the substance undergoing measurement 4 is observed distinctly with high temporal resolution. By fitting, for example, an exponential function to this graph, the lifetime of the fluorescence that is the subject of the measurement can be calculated.

Moreover, regarding the movement of the gate pulse $l_g$ through the detection medium 6, by making the gate pulse $1_g$ propagate in a filament shape extending over a long distance, the spatial resolution and the temporal resolution can be further improved, and moreover the uniformity of the signal in the time axis direction can be improved. In the example described above, a focusing lens 25a that is a long-focal-length plano-convex lens of focal length 200 mm is used as the incidence optical system for making the gate pulse $l_g$ be incident on the detection medium 6.

As a result, propagation is realized in a state of a filament shape under conditions in which the beam diameter of the gate pulse $l_g$ in the observed light track region (light distribution) is small, and there are no great changes in the beam diameter. In this case, the time of interaction with the fluorescence $l_p$ becomes short, and the optical excitation density becomes uniform, and hence the temporal resolution of the measurement of the fluorescence $l_p$ using the computed image described above is further improved. Moreover, the reliability of the measurement is improved, with for example correction, compensation and so on of the measurement results by image processing becoming unnecessary. Note that, with regard to the focal length of the above-mentioned focusing lens 25a, a constitution may also be adopted in which a convex lens of yet longer focal length is used and hence the measurement precision is yet further improved.

Note that, with regard to the variable optical delayer 21, which is means for changing the mutual timing between the light pulses, a constitution in which a variable optical delayer is installed in the excitation optical system 3 instead of in the gate optical system 2, or a constitution in which a variable optical delayer is installed in both of the optical systems 2 and 3 may be adopted. Moreover, in the case that observation of the fluorescence and the change over time thereof is carried out only with a certain specific timing, and it is not necessary to change the time origin, a constitution in which there is no timing adjustment means such as a variable optical delayer may be adopted.

Moreover, regarding the adjustment and changing of the measurement conditions such as the state of focusing of the gate pulse $l_g$, for example in the example shown in FIG. 2, this can also be realized by making the focusing lens 25a, which is the incidence optical system, be a movable optical system having a constitution such that movement is possible in the direction of the optical axis, whereby the reliability of the measurement can be further improved.

Regarding the detection medium 6, in the example shown in FIG. 2 air is used, but another substance capable of giving rise to a nonlinear optical effect may also be used as the detection medium 6. In particular, it is preferable to use a substance comprising a gas or a liquid as the detection medium 6. In this case, the response speed of the nonlinear optical effect of the gas or liquid is generally faster than in the case of a solid, and hence observation with higher temporal resolution becomes possible. For example, $CS_2$ (a liquid at normal temperature) can be used as the detection medium instead of air. In this case, the response speed is slower than with air, but observation can be carried out with the intensity of the gate pulse reduced.

Moreover, it is preferable to use as the detection medium 6 a substance for which the birefringence due to the change in the refractive index induced after the gate pulse has passed through vanishes faster than 1 picosecond. As a result, it becomes possible to make the temporal resolution of the measurement be in the femtosecond range. Such a condition is more easily satisfied the simpler the structure, and hence for example a noble gas is suitable as the detection medium 6 for improving the temporal resolution.

Note that preferable conditions on the substance used as the detection medium include (1) the substance has sufficient transmissivity at the wavelength of the incident light pulse, (2) the nonlinear optical effect for the polarized component of the gate pulse perpendicular to the detection plane is large and the response is fast, (3) the polarization state of the fluorescence is not disturbed, (4) there is no dispersion such as to greatly change the pulse width of the incident light, and (5) the substance has sufficient resistance to the light energy of the incident light.

As the method of installing the detection medium, in the example of FIG. 2, a constitution is adopted in which the apparatus as a whole is installed in air, which acts as the detection medium, but various methods other than this installation method can be envisaged. For example, there is a method in which an enclosure is installed for a region including a prescribed region into which the gate pulse $l_g$ is incident and the fluorescence $l_p$ is irradiated and also part of the apparatus other than this, and the inside of this enclosure is filled with the detection medium.

The region where the enclosure is installed can be, for example, the region 60a or 60b shown by the dashed lines in FIG. 2, or can be set to be a region other than this. In this case, out of the enclosure, it is preferable for the material used for constituting at least the parts where the incidence, irradiation or exiting of light is carried out to satisfy the above-mentioned conditions that are preferable for the detection medium.

Figure 4:
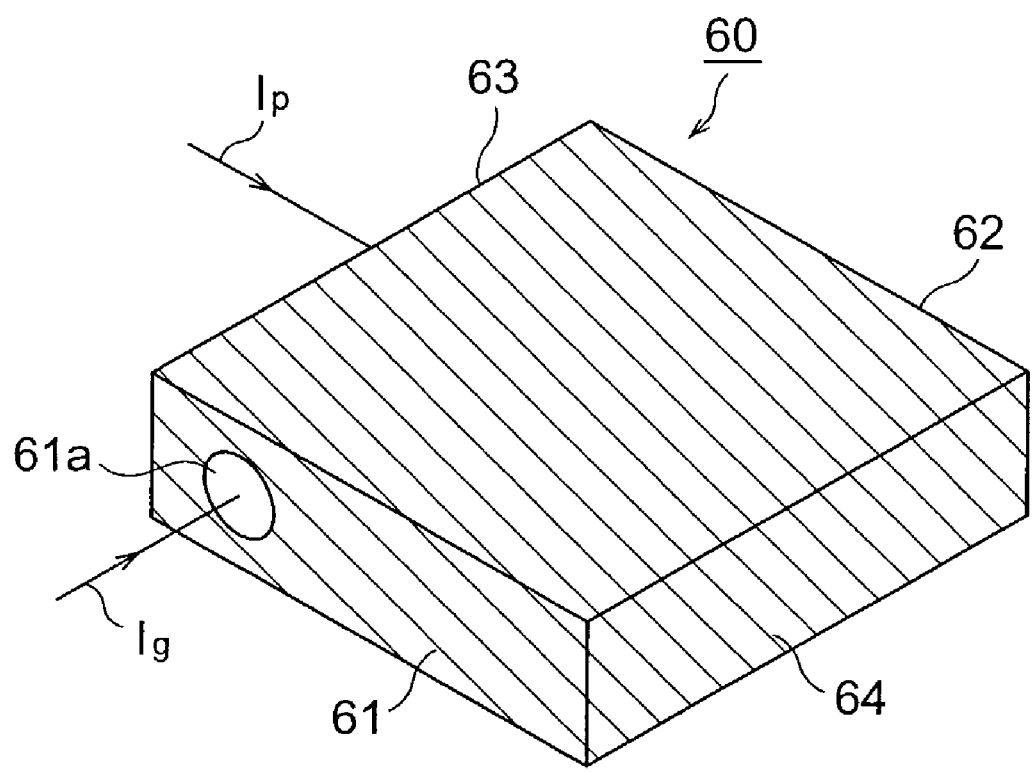
FIG. 4 is a perspective view showing an example of an enclosure used for the detection medium.

Regarding the enclosure in this case, as with the enclosure 60 shown in FIG. 4, which is an example of the enclosure, to reduce the influence of background light, it is preferable for parts other than the parts where the incidence, irradiation or exiting of light is carried out to be painted black or the like (the parts in FIG. 4 with diagonal lines). Moreover, the parts where the incidence, irradiation or exiting of light is carried out are, for example, formed as windows comprising quartz glass or the like having an antireflective film applied to both surfaces thereof.

FIG. 4 shows an enclosure 60 that can be used in the case that all of the photodetection part is contained inside the enclosure as with the region 60b shown in FIG. 2; an incidence window 61a formed in a gate pulse incidence surface 61 is shown. Moreover, an irradiation window (not shown) is similarly formed in a fluorescence irradiation surface 63. In the case that part of the photodetection part is installed outside the enclosure 60 as with the region 60a shown in FIG. 2, it is necessary to further provide an exiting window in a fluorescence exiting surface 64. Moreover, a constitution in which a gate pulse exiting surface 62 has an exiting window may also be adopted if necessary. Moreover, in the case that degeneration of the detection medium during observation is a problem, for example in the case that the region where the enclosure is installed is small, it is preferable to adopt a constitution in which a pump or the like is connected in and the detection medium is circulated.

If the detection medium is a gas, then the parts where the incidence, irradiation or exiting of a light pulse is carried out can be made to be openings instead of windows. In this case, it is necessary to continuously feed the gas, which is the detection medium and which is discharged from the openings, into the enclosure from a gas cylinder via a hose or the like.

Moreover, in the case of using a harmless gas as the detection medium, it is also possible to not use an enclosure, but rather put the outlet of a hose connected to a gas cylinder or the like in a prescribed position near to the region of the detection medium, feed in the gas by jetting the gas into this region, and use this as the detection medium. In this case, there will be somewhat of a disadvantage in terms of the purity of the gas, but there will be advantages in that implementation will be easy and the apparatus will be simplified, and moreover problems such as absorption or reflection of light by windows will not arise.

Furthermore, there is also a method in which a cell filled with the gas or liquid that acts as the detection medium is installed in the region of the detection medium and used as the detection medium. This method is suitable in particular in the case of using a liquid, or a gas that is difficult to handle such as a poisonous gas. Moreover, the amount of the detection medium used can be made reduced. In this case, as in the case of an enclosure, it is preferable for the vessel used for constituting the cell to satisfy the above-mentioned conditions that are preferable for the detection medium.

Figure 5A:
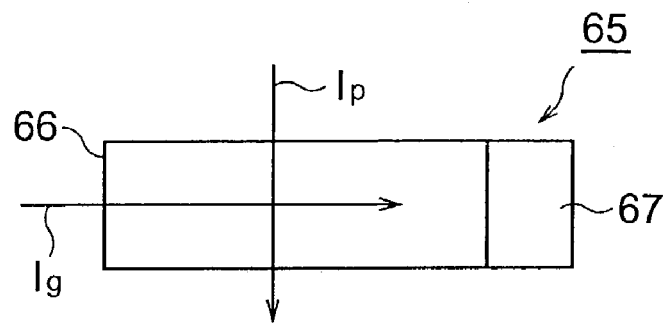
FIGS. 5A and 5B are a top view and a side view showing an example of a cell used for the detection medium.
Figure 5B:
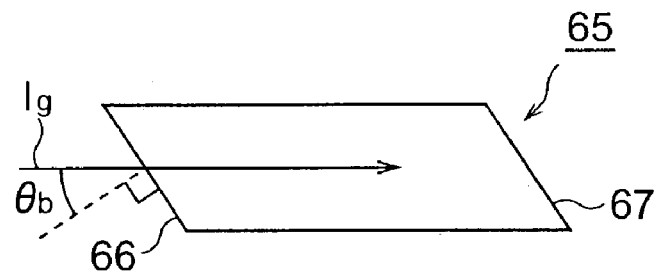

In this case, with the direction of polarization of the incident light having been established, as with the cell 65 shown in FIG. 5A (top view) and FIG. 5B (side view), which is an example of the cell, it is preferable for a gate pulse incident surface 66 or a gate pulse exiting surface 67 to be formed such that the normal thereto (shown as a dashed line in FIG. 5B) is at the Brewster angle $\theta_b$ relative to the optical axis. As a result, regarding the gate pulse incidence surface 66, reflection can be suppressed, and hence the transmissivity can be increased. Moreover, regarding the gate pulse exiting surface 67, light being reflected at the exiting end surface of the cell and going back into the detection medium can be suppressed, and hence the precision of the measurement can be increased. This is particularly effective in the case that a liquid, for which the occurrence of bubbles in the detection medium is a problem, is used, since the scattering of reflected light by the bubbles can be prevented.

Note that when using the Brewster angle as described above for the incidence surface and the exiting surface of the gate pulse $l_g$, in the case in particular that a liquid is used as the detection medium, the refractive index is greatly different to that of air, and hence it is necessary to set the optical path while considering the change in the direction of travel of the gate pulse $l_g$.

Figure 6A:
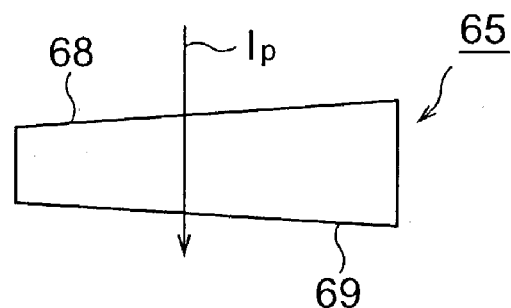
FIGS. 6A and 6B are top views showing other examples of the cell used for the detection medium.
Figure 6B:
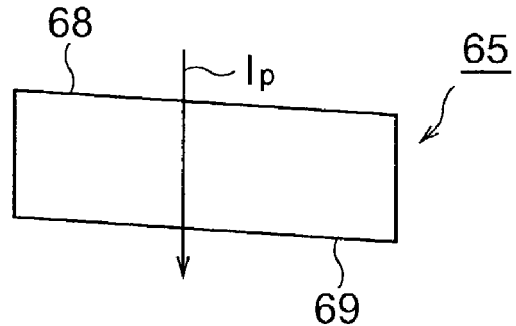

Moreover, it is preferable for an antireflective film to be applied onto the irradiation surface and the exiting surface of the fluorescence $l_p$. Moreover, as shown by the examples in the top views of FIG. 6A and FIG. 6B, it is also possible to form the fluorescence irradiation surface 68 and the fluorescence exiting surface 69 inclined to the horizontal direction or the like so that reflection is suppressed, this being within a range for which there is no influence on the polarization state of the fluorescence $l_p$, whereby when viewed from above the cell becomes a trapezoidal shape (FIG. 6A), a parallelogrammic shape (FIG. 6B) or the like. In this case as well, the optical path is set while considering the change in the direction of travel of the light pulse.

In the case of using a cell in this way, two taps should be installed in the upper part or the like so that the gas or liquid that is the detection medium can be replaced, circulated or the like as appropriate. Moreover, in the case in particular that the detection medium is made to be a gas, as a method of increasing the purity thereof, a method can be used in which the inside of the cell is first put into a vacuum state from one of the taps, and then after this tap has been closed, the gas is filled in from the other tap. Note that regarding the shape of the cell, there is no limitation to the above, but rather various shapes and constitutions can be adopted in accordance with various conditions such as the energies, polarization states and optical paths of the light pulses.

It is preferable for the pulse light source 11 to be a pulse laser for which the pulse width of the outputted light pulse is shorter than 1 picosecond. As a result, and also by selecting a detection medium for which measurement with high temporal resolution is possible such as a noble gas as described above, it becomes possible to make the temporal resolution of the measurement be in the femtosecond range. Furthermore, it is preferable to use a pulse laser having optical amplification means that increases the peak power of the outputted light pulse. An optical amplification method is known for lasers having a short pulse width, and by using this to obtain a light pulse having an extremely high peak power, the degree of freedom of the constitution of the apparatus becomes greater, for example it becomes possible to use even a substance having a small nonlinear optical effect as the detection medium.

Moreover, if a substance for which breakdown occurs through the incident gate pulse is used as the detection medium, and for example a light pulse having a large peak power as mentioned above is condensed and made to be incident on the detection medium, then breakdown of the substance can be brought about easily. In this case, it becomes possible to utilize this to further improve the temporal resolution of the measurement. That is, breakdown is made to occur in the detection medium through the high-intensity gate pulse, and an unwanted component that is late in time out of the fluorescence arriving at each position in the detection medium is absorbed by the plasma induced through the breakdown. As a result, the time width of the fluorescence arriving at the photodetection means is restricted, and hence the temporal resolution can be further improved.

Moreover, as the photodetection means such as the camera 73, by using photodetection means having a function of suppressing dark noise such as a cooled CCD camera, the efficiency of the detection of light and the measurement precision can be further improved. As a result, observation becomes possible even with faint fluorescence or the like.

Figure 7:
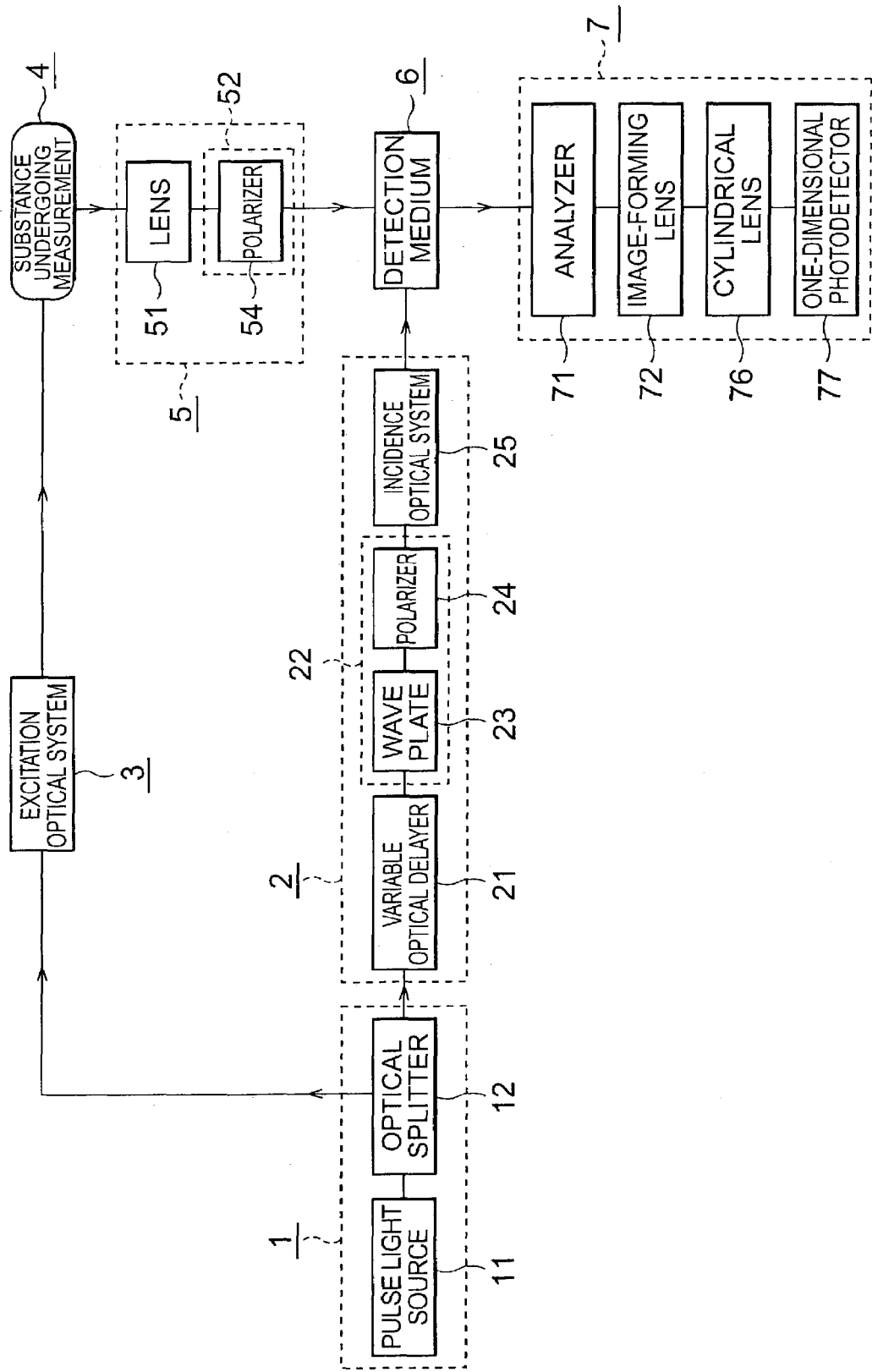
FIG. 7 is a block diagram showing a second embodiment of the fluorescence lifetime measuring apparatus.

FIG. 7 is a block diagram showing a second embodiment of the fluorescence lifetime measuring apparatus according to the present invention. The fluorescence lifetime measuring apparatus in the present embodiment is the same as the first embodiment with regard to the light source part 1, the gate optical system 2, the excitation optical system 3, and the detection medium 6. On the other hand, in the fluorescence optical system 5, in addition to the polarizer 54, a lens 51 is further installed immediately downstream of the substance undergoing measurement 4. As a result, the fluorescence generated by the substance undergoing measurement 4 can be efficiently concentrated and then led to the light track region in the detection medium 6 where the measurement of the fluorescence is carried out. Here, to prevent dropping of the temporal resolution, it is necessary to design the optical system such that there is sufficiently little aberration.

Moreover, regarding the photodetection part 7, a cylindrical lens 76, which is optical image conversion means that converts the two-dimensional optical image of the transmitted fluorescence into a one-dimensional optical image, and a one-dimensional photodetector 77 for detecting the one-dimensional optical image produced by the cylindrical lens 76 are installed downstream of the analyzer 71 and the image-forming lens 72. In particular, by installing the cylindrical lens 76 so as to focus the transmitted fluorescence in a direction perpendicular to the axis of incidence of the excitation pulse and thus form a one-dimensional optical image on the one-dimensional photodetector 77, it becomes possible to obtain information on the change over time in the fluorescence as shown in FIG. 3 more efficiently.

Figure 8:
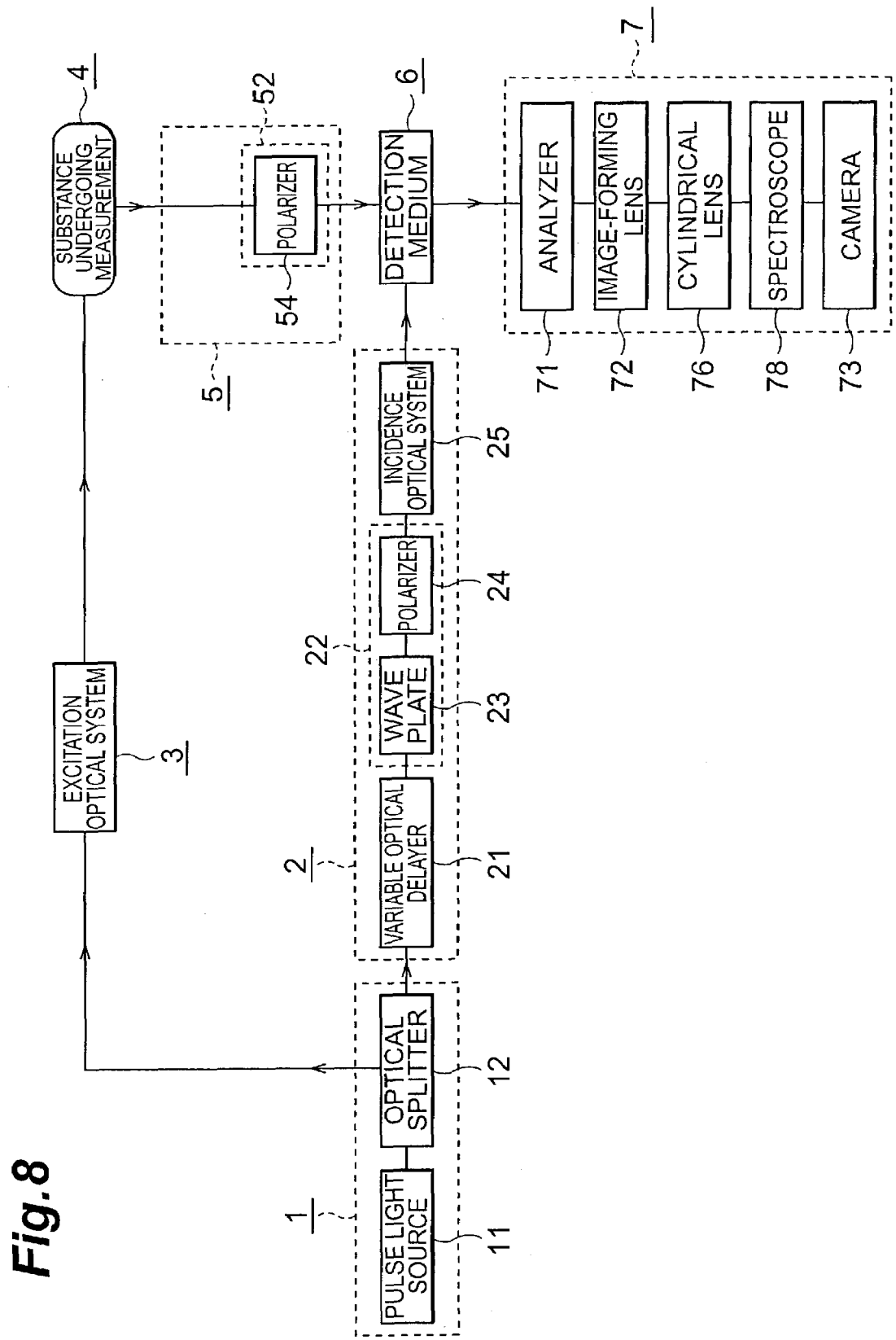
FIG. 8 is a block diagram showing a third embodiment of the fluorescence lifetime measuring apparatus.

FIG. 8 is a block diagram showing a third embodiment of the fluorescence lifetime measuring apparatus according to the present invention. The fluorescence lifetime measuring apparatus in the present embodiment is the same as the first embodiment with regard to the light source part 1, the gate optical system 2, the excitation optical system 3, the fluorescence optical system 5, and the detection medium 6. On the other hand, with regard to the photodetection part 7, a cylindrical lens 76 is used as optical image conversion means as in the second embodiment, and moreover a spectroscope 78 is installed downstream of the cylindrical lens 76. According to this constitution, the one-dimensional optical image produced by the cylindrical lens 76 is incident on the incidence slit of the spectroscope 78 and is spectrally separated, and the position of formation of the image outputted from the spectroscope 78 is made to coincide with the light-receiving plane of the camera 73, and hence the two-dimensional image outputted from the spectroscope 78 is observed by the camera 73.

Figure 9:
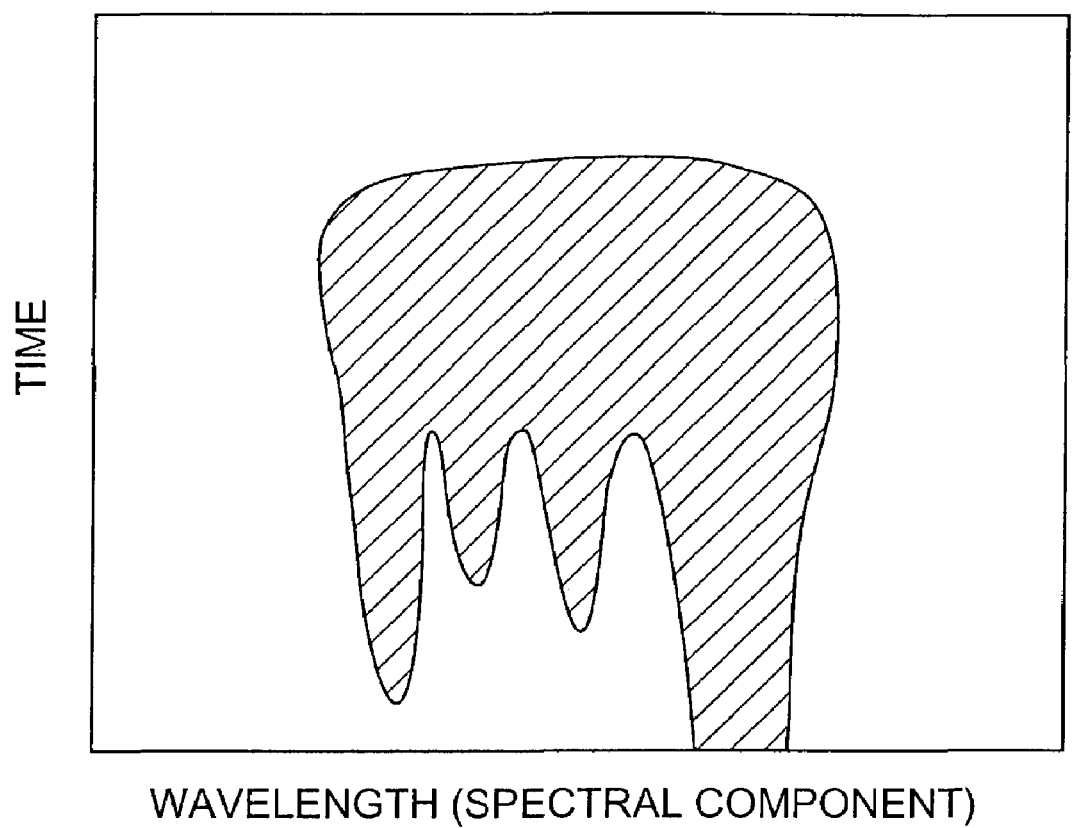
FIG. 9 is a drawing showing a fluorescence image observed using the fluorescence lifetime measuring apparatus shown in FIG. 8.

By carrying out the measurement with spectral separation in this way, it becomes possible to obtain information on the change over time in each of the wavelength components (spectral components) of the fluorescence. An example of the observed image, i.e. the measurement results, obtained using such a constitution is shown in FIG. 9. The horizontal axis is the wavelength, which corresponds to the spectral components, and is obtained through the spectral separation described above. Moreover, the vertical axis shows the arrival time of the fluorescence, which is obtained through position-time conversion as with the horizontal axis of the graph shown in FIG. 3.

From such two-dimensional measurement results, information on the change over time can be obtained for each spectral component of the fluorescence. For example, by cutting out the section of the two-dimensional intensity distribution shown in FIG. 9 for a particular wavelength, and thus creating a one-dimensional intensity distribution against time (which corresponds to the position in the time axis direction), which is the vertical axis, an intensity distribution for a particular spectral component as shown in FIG. 3 can be obtained for each spectral component. Note that to improve the measurement precision, it is preferable to obtain the spectrum of the fluorescence in advance, and for example filter the observed image obtained.

Figure 10:
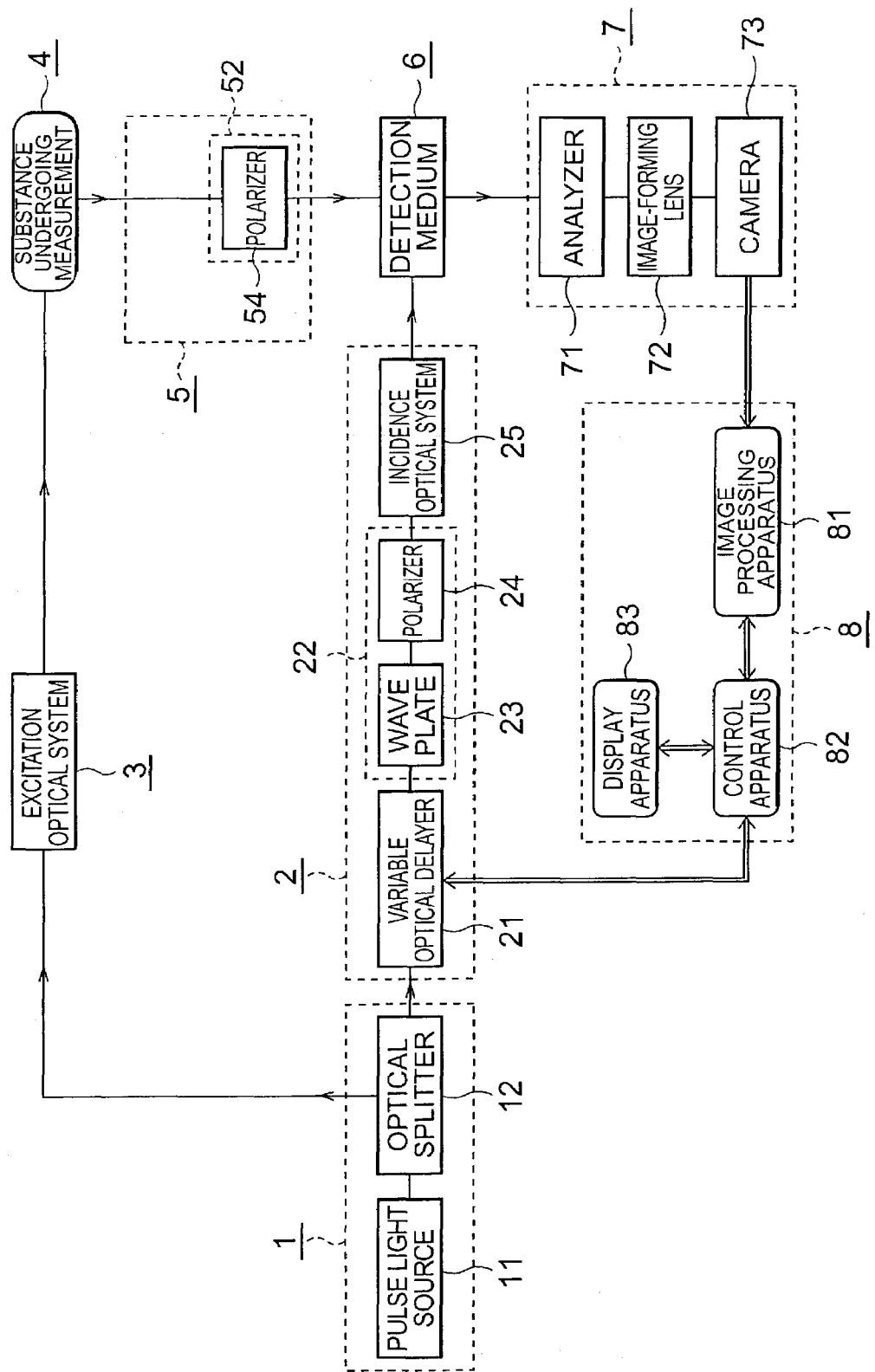
FIG. 10 is a block diagram showing a fourth embodiment of the fluorescence lifetime measuring apparatus.

FIG. 10 is a block diagram showing a fourth embodiment of the fluorescence lifetime measuring apparatus according to the present invention. The fluorescence lifetime measuring apparatus in the present embodiment is the same as the first embodiment with regard to the constitution of the apparatus, but a control part 8 that carries out control of the various parts of the apparatus, calculations on the image data, and so on is further installed. This control part 8 has an image processing apparatus 81, a control apparatus 82, and a display apparatus 83.

The image processing apparatus 81 is connected to the CCD camera 73, and organization and analysis of observed images picked up by the CCD camera 73, required calculations and so on are carried out by the image processing apparatus 81. For example, subtraction of image data between when the fluorescence is irradiated and not irradiated as described earlier with regard to the example shown in FIG. 2, production of graphs as shown in FIG. 3 and so on can be achieved by carrying out analysis after obtaining image data using the CCD camera 73. In contrast, by connecting the CCD camera 73 to the image processing apparatus 81 as shown in FIG. 10, it becomes possible to carry out such image processing in real time during measurement.

The image processing apparatus 81 is further connected to the control apparatus 82, which is for controlling the apparatus as a whole. The control apparatus 82 carries out acquisition of image data and so on via the image processing apparatus 81, display of the obtained data by using the display apparatus 83, and so on. Moreover, the control apparatus 82 is connected to the variable optical delayer 21, and can thus control the time delay while correlating the time delay with the observations. Moreover, if necessary a constitution may be adopted in which the control apparatus 82 is further connected to the pulse light source 11 and so on.

Moreover, according to results of carrying out observations, it was found that with the apparatus shown in FIG. 2, the intensity of the transmitted fluorescence is approximately proportional to the square of the intensity of the gate pulse, and thus that observation is possible primarily through an optical Kerr effect that arises in the detection medium 6. In this case, the image data for the observed image obtained corresponds to the distribution of the square of the intensity of the gate pulse at each time. Consequently, in the image processing apparatus 81 described above, by taking the square root of the intensity of the image data for each pixel or further carrying out an operation such as arcsin when producing the observed image, it is possible to obtain an observed image that more accurately reflects the spatial distribution of the intensity of the light pulse.

Figure 11:
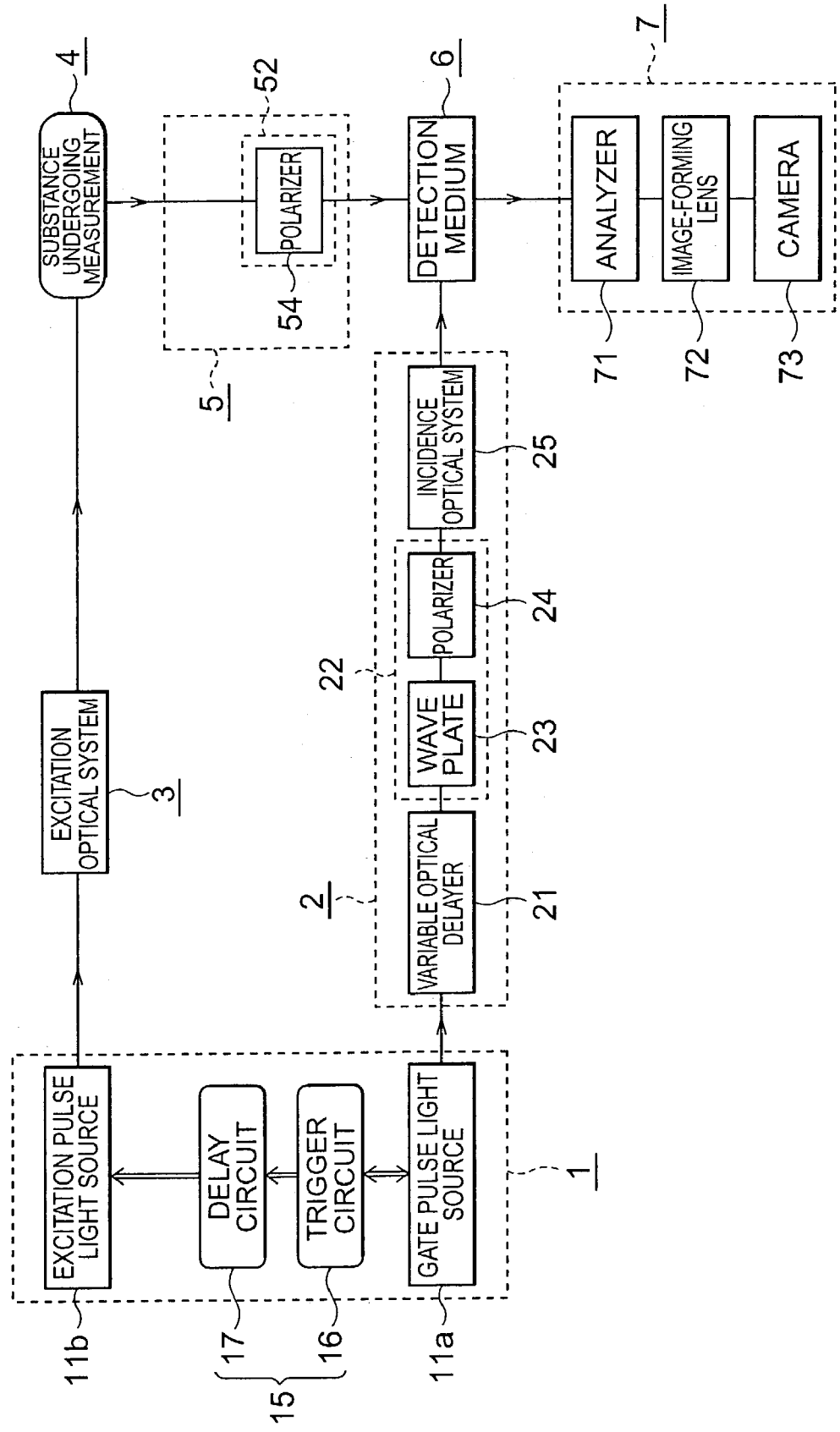
FIG. 11 is a block diagram showing a fifth embodiment of the fluorescence lifetime measuring apparatus.

FIG. 11 is a block diagram showing a fifth embodiment of the fluorescence lifetime measuring apparatus according to the present invention; here, a single pulse light source is not used as the light source part 1, but rather a separate gate pulse light source 11*a* and excitation pulse light source 11*b* are used respectively for the gate pulse for measuring fluorescence and the excitation pulse for producing the fluorescence.

The timing of the excitation pulse, i.e. the timing of the fluorescence produced by the excitation pulse, relative to the gate pulse is controlled by a timing control circuit 15 in addition to the variable optical delayer 21. The timing control circuit 15 has a trigger circuit 16 and a delay circuit 17; using these, the two pulses can be synchronized, and moreover setting and changing of the time delay difference can be carried out. In this case, a constitution may be adopted in which neither the gate optical system 2 nor the excitation optical system 3 has a variable optical delayer.

Moreover, in the case of using two light sources in this way, the pulse width and the wavelength can be made to be different for the gate pulse and the excitation pulse. By selecting these, it thus becomes possible, for example, to realize a further improvement in the temporal resolution.

Figure 12:
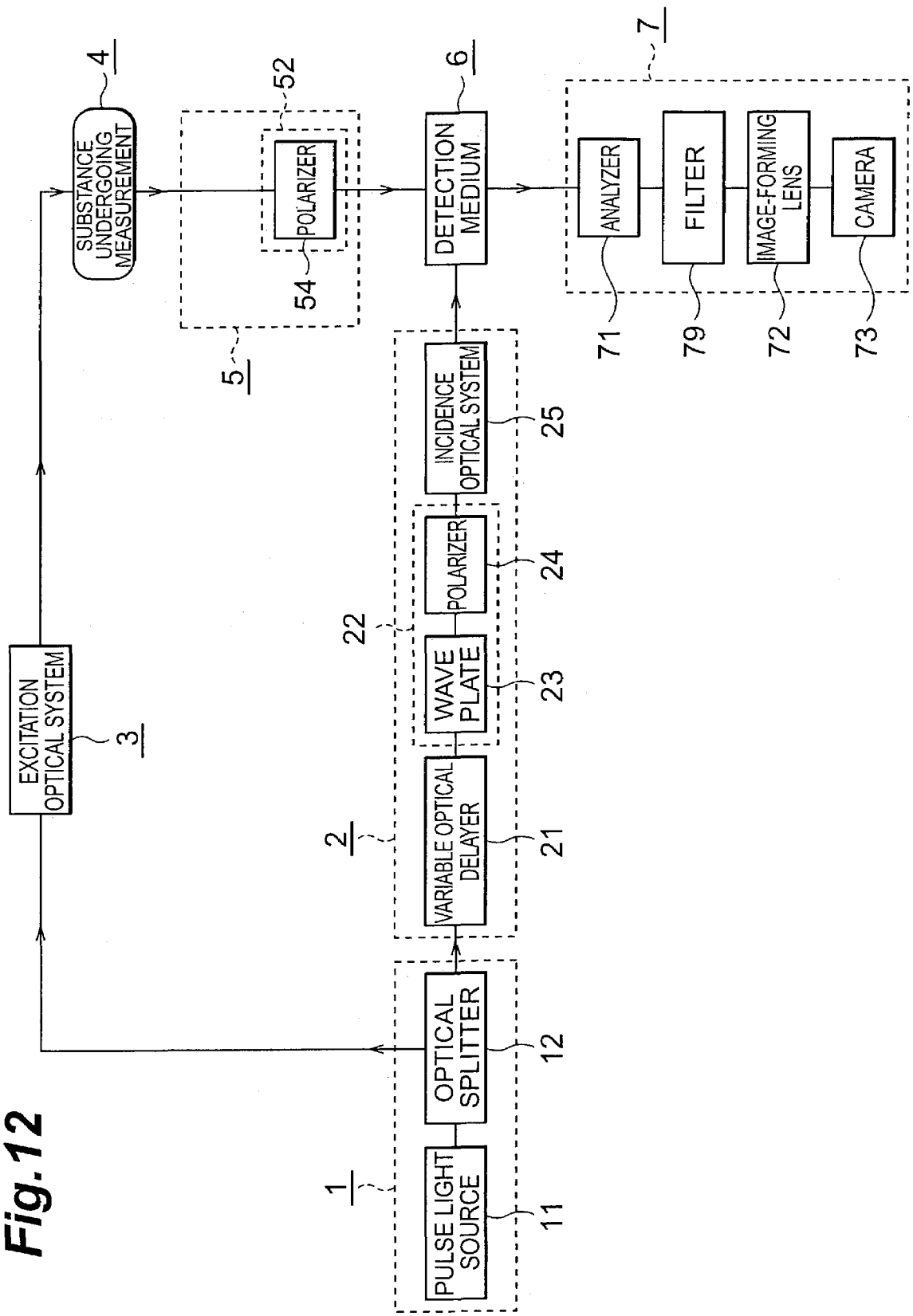
FIG. 12 is a block diagram showing a sixth embodiment of the fluorescence lifetime measuring apparatus.

FIG. 12 is a block diagram showing a sixth embodiment of the fluorescence lifetime measuring apparatus according to the present invention. The fluorescence lifetime measuring apparatus in the present embodiment is the same as the first embodiment with regard to the light source part 1, the gate optical system 2, the fluorescence optical system 5, and the detection medium 6. On the other hand, with regard to the excitation optical system 3, a constitution is adopted in which the direction of the axis of incidence of the excitation pulse incident on the substance undergoing measurement 4 is approximately on the same axis as the direction of the axis of exiting of the fluorescence exiting from the substance undergoing measurement 4 toward the fluorescence optical system 5 and the detection medium 6.

In the case that the axis of incidence of the excitation pulse and the axis of exiting of the fluorescence are on different axes such as approximately orthogonal to one another, for example as in the embodiment shown in FIG. 1 and FIG. 2, the excitation pulse that has passed through the substance undergoing measurement 4 can be removed from the axis of exiting of the fluorescence. However, the cross-sectional shape of the fluorescence generating region formed in the substance undergoing measurement 4 is spread out in the direction of the axis of exiting of the fluorescence in correspondence with the beam cross-sectional shape of the excitation pulse, and hence a difference in optical path length arises with regard to the fluorescence generated at different places being led to the detection medium 6.

In contrast, by making the axis of incidence of the excitation pulse and the axis of exiting of the fluorescence be approximately the same axis as in the present embodiment, the beam cross section direction of the excitation pulse becomes a direction perpendicular to the axis of exiting of the fluorescence, and hence the optical path length difference is reduced. In this case, because the difference in the time taken to guide the fluorescence from different places in the fluorescence generating region in the substance under going measurement 4 to the detection medium 6 is reduced, the temporal resolution of the measurement can be increased.

In the case of adopting such a constitution, the excitation pulse component that has passed through the substance undergoing measurement 4 is also led in the direction of the axis of exiting of the fluorescence, and by also detecting this excitation pulse itself, the time origin of the fluorescence measurement can be determined easily. However, in general the excitation pulse is stronger than the fluorescence that is the subject of the measurement, and hence the efficiency of the measurement of the fluorescence may be reduced by the excitation pulse being incident on the photodetector.

To counteract this problem, in the present embodiment, a filter 79 is inserted downstream of the analyzer 71 of the photodetection part 7 as shown in FIG. 12. This filter 79 cuts out light of a wavelength component used for the excitation pulse. An ordinary colored glass filter can, for example, be used as the filter 79, or a notch filter or the like can be used as a filter that cuts out only the excitation pulse more efficiently.

Either all or part of the excitation pulse may be removed by the filter 79. For example, the time when the excitation pulse arrives at the detection medium 6 is a time reference point for the fluorescence measurement, and hence by leaving behind and detecting part of the excitation pulse, this can be used in the determination of the time origin. Moreover, regarding the position in which the filter is placed, in FIG. 12 the filter is installed within the photodetection part 7, but the filter may also be installed within the fluorescence optical system 5. However, in this case the position of the filter is before the fluorescence is incident on the detection medium 6, and hence it is necessary to use a filter for which dispersion is sufficiently suppressed in the wavelength region that is not absorbed.

Figure 13:
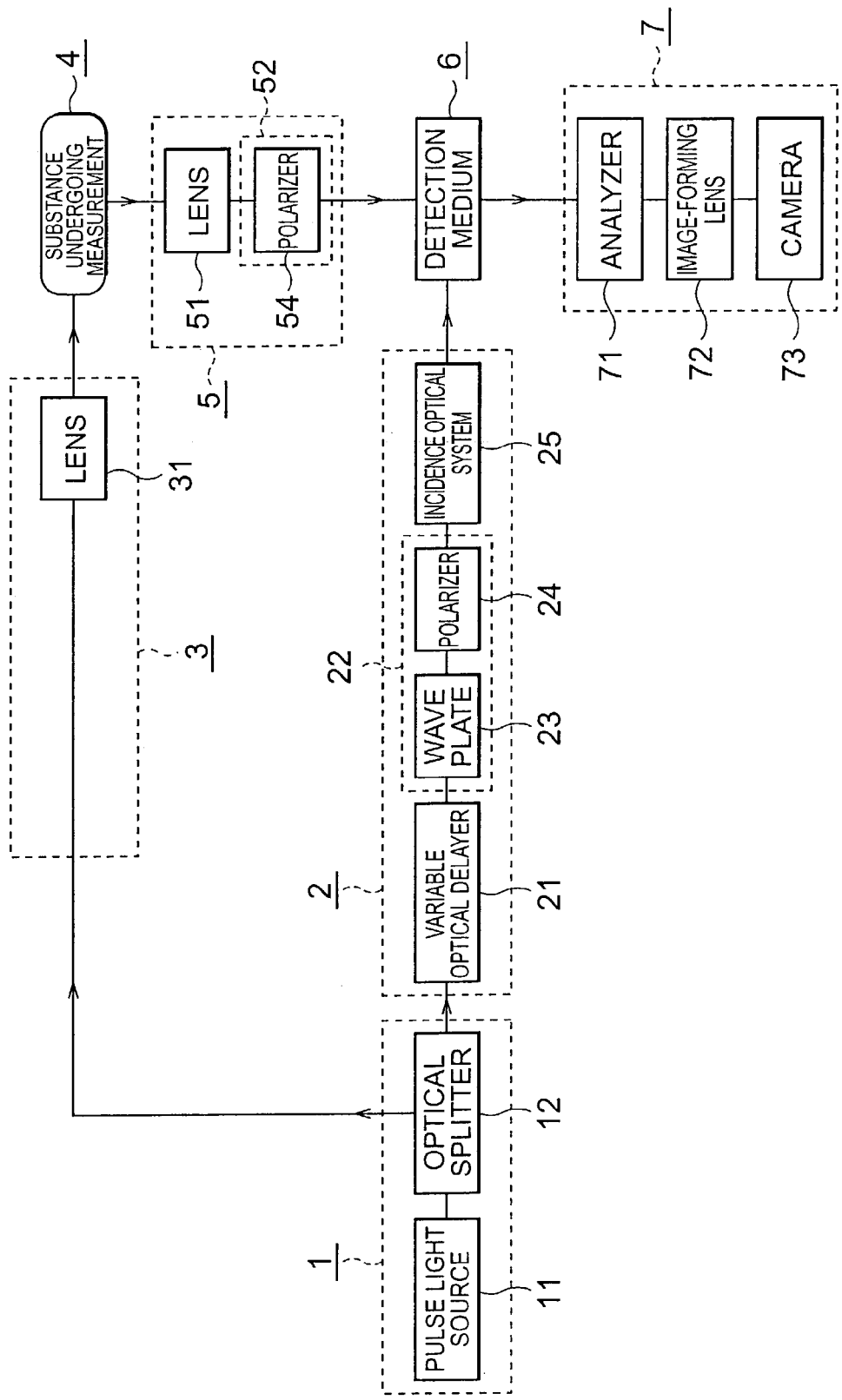
FIG. 13 is a block diagram showing a seventh embodiment of the fluorescence lifetime measuring apparatus.

FIG. 13 is a block diagram showing a seventh embodiment of the fluorescence lifetime measuring apparatus according to the present invention. The fluorescence lifetime measuring apparatus in the present embodiment is the same as the first embodiment with regard to the light source part 1, the gate optical system 2, the detection medium 6, and the photodetection part 7. On the other hand, with regard to the excitation optical system 3, a lens 31 is installed as excitation pulse condensing means so as to form an optical system that focuses the excitation pulse incident on the substance undergoing measurement 4 at a focal point right on the substance undergoing measurement 4. As a result, it becomes such that the fluorescence generating position in the substance undergoing measurement 4 can be regarded as virtually a point light source, and hence the optical path length difference and the light-guiding time difference for the fluorescence into the detection medium 6 caused by the finite spreading out of the beam can be suppressed, and thus the temporal resolution of the measurement is improved.

Here, as the lens 31 it is preferable to use a lens for which there is sufficiently little dispersion that the pulse width of the excitation pulse does not increase. Moreover, it is preferable to use a lens that has been designed such that other aberration is also sufficiently slight. Moreover, an off-axis parabolic mirror, a concave mirror or the like can also be used as the excitation pulse condensing means instead of a lens. With these, chromatic aberration can be reduced more than with a lens, which is important in particular in the case of using light of about 10 femtoseconds or less as the excitation pulse.

Moreover, in the present embodiment, a lens 51 is further installed as fluorescence condensing means in the fluorescence optical system 5. By installing the lens 51 in the fluorescence optical system 5 in this way, the fluorescence from the substance undergoing measurement 4 can be led to the detection medium 6 efficiently, and hence the measurement efficiency can be improved.

Moreover, in the present embodiment, the lens 51 is placed such as to convert the fluorescence exiting from the fluorescence generating position of the substance undergoing measurement 4 into parallel light of even wavefront. As a result, it becomes possible to make the timing at which fluorescence emitted from the substance undergoing measurement 4 at the same time arrives at a position along the axis of propagation of the gate pulse in the detection medium 6 be even, and thus maintain the synchronicity thereof, and hence the temporal resolution of the measurement can be further improved.

Regarding the lens 51, because the fluorescence generally has a broad spectrum, it is preferable in particular to use a lens having little chromatic aberration. Moreover, as with the lens 31, it is preferable to use a lens that has been designed such that other aberration is also sufficiently slight. Moreover, as with the excitation pulse condensing means, it is possible to use an off-axis parabolic mirror, a concave mirror or the like as the fluorescence condensing means other than the lens, with these being effective when a further reduction in chromatic aberration is required.

The fluorescence lifetime measuring apparatus of the present invention is not limited to the embodiments and examples described above, but rather various modifications are possible. For example, wavelength conversion means that changes the wavelength of the gate pulse or the excitation pulse may be installed in the optical path of the gate optical system or the excitation optical system. By using wavelength conversion means in the gate optical system, for example a wavelength for which the temporal resolution is best can be selected and set as the wavelength used in the measurement. Moreover, by using wavelength conversion means in the excitation optical system, it becomes possible to generate fluorescence by exciting the substance undergoing measurement at an excitation wavelength of interest. Examples of such wavelength conversion means include an optical parametric amplifier, a sum/difference frequency generator, and an SHG crystal.

Moreover, it is also possible to install waveform conversion means that changes the waveform or the like of the excitation pulse in the optical path of the excitation optical system, and thus generate and observe the change over time in fluorescence due to various time waveforms. Examples of waveform conversion means are disclosed for example in Japanese Patent Application Laid-open No. H10-206234, and include a pulse train generator and a waveform generator. Out of these, a pulse train generator for example converts a light pulse into a pulse train, with it being possible to use an etalon or the like. Moreover, a waveform generator changes the state of the waveform or the like of a light pulse, with it being possible to use a spatial light modulator or the like.

Moreover, spatial distribution conversion means that changes the spatial distribution of the gate pulse or the excitation pulse may be installed in the gate optical system or the excitation optical system. Various types of such spatial distribution conversion means can be used, for example a slit-shaped mask having a slit of a prescribed width. By controlling the spatial shape of the gate pulse or the excitation pulse using such spatial distribution conversion means, the measurement conditions can be controlled in accordance with other conditions, the purpose of the measurement and so on, and hence it becomes possible, for example, to realize measurement conditions for which the temporal resolution of the measurement is increased.

That is, in the case that a slit-shaped mask is installed in the gate optical system such that the longitudinal direction of the slit is a direction perpendicular to the detection plane (i.e. perpendicular to the axis of incidence of the gate pulse and the axis of irradiation of the fluorescence), spreading of the gate pulse in the direction of the axis of irradiation of the fluorescence in the detection medium 6 is reduced. In this case, the passage time taken for the fluorescence to pass through the region of the gate pulse, i.e. the time that each fluorescence component interacts with the gate pulse, becomes shorter, and hence the width in the direction of the axis of propagation of the gate pulse of the optical image due to the fluorescence that passed through the detection medium 6 at a particular time is reduced. As a result, the temporal resolution of the measurement can be improved.

Moreover, in the case that a slit-shaped mask is installed in the excitation optical system, the cross section of the excitation pulse incident on the substance undergoing measurement 4 is reduced, and hence as in the case for example that condensing is carried out using a lens, the temporal resolution of the measurement can be increased through reduction of the optical path length difference. In addition to the above, control of the measurement conditions can be carried out using various other spatial distribution conversion means.

Note that regarding the guiding of light through each of the optical systems, a constitution may be adopted in which an optical fiber or the like is used. However, in the case that an optical fiber is used, the pulse width of the light pulse broadens due to the dispersion of the optical fiber, and hence the temporal resolution of the fluorescence measurement deteriorates. It is thus preferable to adopt a constitution so as to correct the broadening of the pulse width by using a dispersion shifting fiber, a grating fiber, a diffraction grating pair, a prism pair or the like.

Observation and measurement of fluorescence and the change over time thereof using the fluorescence lifetime measuring apparatus according to the present invention can be applied to various substances undergoing measurement. Moreover, there is no limitation to fluorescence in the normal sense, but rather broad application is possible to various types of measurement, thermodynamic observation and control, and so on, for example by increasing the intensity of the excitation pulse and thus bringing about ablation in the substance undergoing measurement, the ablation process of the substance can be measured.

INDUSTRIAL APPLICABILITY

The present invention can be used as a fluorescence lifetime measuring apparatus according to which observation of a fluorescence phenomenon and measurement of the fluorescence lifetime can be carried out efficiently with high temporal resolution. In particular, two synchronized light pulses outputted from an ultra-short pulse laser or the like are used, and one of these light pulses is put into a prescribed polarization state, and is made to be incident on a detection medium as a gate pulse used in the fluorescence observation. The other light pulse is made to be incident on a substance undergoing measurement as an excitation pulse to excite fluorescence in the substance undergoing measurement, and this fluorescence is irradiated onto the detection medium to obtain a fluorescence image. As a result, measurement of the change over time in the fluorescence with high temporal resolution, and hence determination of the fluorescence lifetime and so on with high temporal resolution become possible.

As the measurement method, a prescribed substance is used as the detection medium, and utilizing a change in refractive index due to a nonlinear optical effect arising in a region of the detection medium where the gate pulse light is distributed (the light track region), a fluorescence image is detected through a change in the polarization state of the fluorescence. Here, the light track region due to the gate pulse propagates with time, and hence the change over time in the fluorescence is made to correspond to a change in position, and thus direct observation using a photodetector such as a CCD camera becomes possible.

What is claimed is:

1. A fluorescence lifetime measuring apparatus, comprising:
    a light source part that produces, from one or more light pulses supplied by one or more pulse light sources, and outputs a first light beam and a second light beam having output timing synchronized with one another;
    a detection medium that exhibits birefringence in a pulse position of a light pulse in accordance with the intensity thereof;
    a gate optical system that forms a gate pulse based on said first light beam, and causes said gate pulse to be incident on said detection medium;
    an excitation optical system that forms an excitation pulse based on said second light beam, and causes said excitation pulse to be incident on a substance undergoing measurement, to generate fluorescence;
    a fluorescence optical system that irradiates said fluorescence from said substance undergoing measurement onto a prescribed region of said detection medium that includes a light track region in which a change in refractive index has been induced through a nonlinear optical effect due to said gate pulse being incident on said detection medium; and
    a photodetection part that detects said fluorescence that has passed through the prescribed region of said detection medium;
    wherein said gate optical system comprises gate pulse polarizing means for putting said gate pulse into a prescribed polarization state, and an incidence optical system that causes said gate pulse to be incident on said detection medium according to prescribed incidence conditions;
    said fluorescence optical system comprises fluorescence polarizing means for putting said fluorescence into a prescribed polarization state;
    and said photodetection part comprises analyzing means that transmits only a prescribed polarized component out of said fluorescence that has passed through the prescribed region of said detection medium, photodetection means that detects and observes said fluorescence that has been transmitted through said analyzing means, and image-forming means that forms said fluorescence that has passed through the prescribed region of said detection medium and been transmitted through said analyzing means into an image on said photodetection means to produce a fluorescence image; whereby the change over time in said fluorescence is measured from said fluorescence image by utilizing the movement with time of the pulse position where birefringence is exhibited in said light track region.

2. The fluorescence lifetime measuring apparatus according to claim 1, characterized in that said light source part comprises a single pulse light source that outputs a light pulse, and optical splitting means that splits said light pulse to produce said first light beam and said second light beam.

3. The fluorescence lifetime measuring apparatus according to claim 1, characterized in that said light source part comprises a gate pulse light source that outputs a light pulse that becomes said first light beam, an excitation pulse light source that outputs a light pulse that becomes said second light beam, and timing control means that synchronizes the output timing of said first light beam and said second light beam.

4. The fluorescence lifetime measuring apparatus according to claim 1, characterized in that one of said gate optical system and said excitation optical system comprises variable optical delay means for setting and changing an optical path length difference between said gate optical system and said excitation optical system.

5. The fluorescence lifetime measuring apparatus according to claim 1, characterized in that said incidence optical system has a movable optical system the position of which is movable on the optical path direction.

6. The fluorescence lifetime measuring apparatus according to claim 1, characterized in that at least one of said gate pulse polarizing means and said fluorescence polarizing means contains a wave plate or a polarizer, and the polarization states of said gate pulse and said fluorescence are each set to be prescribed linear polarization;
 the axis of irradiation of said fluorescence onto said detection medium is within a plane that contains the axis of incidence of said gate pulse onto said detection medium and is perpendicular to the axis of linear polarization of said gate pulse, and the axis of linear polarization of said fluorescence is set to be inclined by 45° to said plane;
 and said analyzing means transmits, out of said fluorescence that has passed through the prescribed region of said detection medium, only a polarized component that is orthogonal to the linear polarization of said fluorescence irradiated onto said detection medium.

7. The fluorescence lifetime measuring apparatus according to claim 1, characterized in that the irradiation angle of said axis of irradiation of said fluorescence relative to said axis of incidence of said gate pulse is 90°.

8. The fluorescence lifetime measuring apparatus according to claim 1, characterized in that said photodetection part further comprises optical image conversion means that converts a two-dimensional optical image of said fluorescence that has passed through the prescribed region of said detection medium into a one-dimensional optical image, and said photodetection means comprises a one-dimensional photodetector.

9. The fluorescence lifetime measuring apparatus according to claim 1, characterized in that said photodetection part further comprises optical image conversion means that converts a two-dimensional optical image of said fluorescence that has passed through the prescribed region of said detection medium into a one-dimensional optical image, and spectroscopic means that is installed between said optical image conversion means and said photodetection means.

10. The fluorescence lifetime measuring apparatus according to claim 1, characterized in that at least one of said gate optical system and said excitation optical system comprises wavelength conversion means that changes the wavelength of said gate pulse or said excitation pulse.

11. The fluorescence lifetime measuring apparatus according to claim 1, characterized in that said excitation optical system comprises waveform conversion means that changes the time waveform.

12. The fluorescence lifetime measuring apparatus according to claim 1, characterized in that at least one of said gate optical system and said excitation optical system comprises spatial distribution conversion means that changes the spatial distribution of said gate pulse or said excitation pulse.

13. The fluorescence lifetime measuring apparatus according to claim 12, characterized in that said spatial distribution conversion means is a slit-shaped mask that has a slit of a prescribed shape and makes the spatial distribution of said gate pulse or said excitation pulse into a slit shape using said slit.

14. The fluorescence lifetime measuring apparatus according to claim 1, characterized by comprising image processing means that carries out processing of image data from said photodetection means.

15. The fluorescence lifetime measuring apparatus according to claim 1, characterized in that said detection medium is made of a substance for which birefringence due to a change in refractive index induced by said gate pulse after the incident said gate pulse has passed through vanishes faster than 1 picosecond.

16. The fluorescence lifetime measuring apparatus according to claim 1, characterized in that said detection medium is made of a noble gas.

17. The fluorescence lifetime measuring apparatus according to claim 1, characterized in that said one or more pulse light sources used in said light source part is a pulse laser with which the pulse width of the outputted light pulse is shorter than 1 picosecond.

18. The fluorescence lifetime measuring apparatus according to claim 1, characterized in that said one or more pulse light sources used in said light source part is a pulse laser having optical amplification means that increases the peak power of the outputted light pulse.

19. The fluorescence lifetime measuring apparatus according to claim 1, characterized in that said detection medium is made of a substance for which breakdown occurs through the incident said gate pulse, and is constituted such that an unwanted component of said fluorescence can be absorbed by a plasma induced through said breakdown.

20. The fluorescence lifetime measuring apparatus according to claim 1, characterized in that said photodetection means comprises a photodetector having a function of suppressing dark noise.

21. The fluorescence lifetime measuring apparatus according to claim 1, characterized by being constituted such that said gate pulse is propagated in a long filament shape in said detection medium.

22. The fluorescence lifetime measuring apparatus according to claim 1, characterized in that the axis of incidence of said excitation pulse on said substance undergoing measurement and the axis of exiting of said fluorescence from said substance undergoing measurement are approximately on the same axis.

23. The fluorescence lifetime measuring apparatus according to claim 1, characterized in that at least one of said fluorescence optical system and said photodetection part comprises a filter that partially or totally removes light of the wavelength used for said excitation pulse.

24. The fluorescence lifetime measuring apparatus according to claim 1, characterized in that said excitation optical system comprises excitation pulse condensing means that makes the cross section of said excitation pulse that is incident on said substance undergoing measurement smaller.

25. The fluorescence lifetime measuring apparatus according to claim 24, characterized in that said excitation pulse condensing means is constituted using a condensing optical system formed such that aberration is reduced.

26. The fluorescence lifetime measuring apparatus according to claim 1, characterized in that said fluorescence optical system comprises fluorescence condensing means that guides said fluorescence from said substance undergoing measurement to said detection medium efficiently.

27. The fluorescence lifetime measuring apparatus according to claim 26, characterized in that said fluorescence condensing means is constituted using a condensing optical system formed such that aberration is reduced.

* * * * *